(12) United States Patent
Noda et al.

(10) Patent No.: US 8,221,313 B2
(45) Date of Patent: Jul. 17, 2012

(54) ENDOSCOPE APPARATUS

(75) Inventors: Kenji Noda, Tokyo (JP); Masatsugu Oyama, Tokyo (JP)

(73) Assignee: Olympus Medical Systems Corp. (JP)

( * ) Notice: Subject to any disclaimer, the term of this patent is extended or adjusted under 35 U.S.C. 154(b) by 1023 days.

(21) Appl. No.: 12/180,655

(22) Filed: Jul. 28, 2008

(65) Prior Publication Data

US 2010/0022834 A1    Jan. 28, 2010

(51) Int. Cl.
*A61B 1/12* (2006.01)
(52) U.S. Cl. ........ 600/159; 600/118; 600/156; 600/158; 604/24
(58) Field of Classification Search .......... 600/156–159; 604/23–25, 118
See application file for complete search history.

(56) References Cited

U.S. PATENT DOCUMENTS

| | | | |
|---|---|---|---|
| 4,836,187 A * | 6/1989 | Iwakoshi et al. | 600/157 |
| 6,299,592 B1 * | 10/2001 | Zander | 604/26 |
| 6,309,347 B1 | 10/2001 | Takahashi et al. | |
| 6,402,688 B1 * | 6/2002 | Takami et al. | 600/158 |
| 6,558,317 B2 | 5/2003 | Takahashi et al. | |
| 7,988,656 B2 * | 8/2011 | Uesugi et al. | 604/23 |
| 2001/0039370 A1 | 11/2001 | Takahashi et al. | |
| 2006/0004322 A1 | 1/2006 | Uesugi et al. | |
| 2007/0238929 A1 * | 10/2007 | Aizenfeld et al. | 600/158 |

FOREIGN PATENT DOCUMENTS

| | | |
|---|---|---|
| JP | 2550321 | 10/1997 |
| JP | 11-276429 | 10/1999 |
| JP | 2006-14961 | 1/2006 |
| JP | 2006-167221 | 6/2006 |
| JP | 2006-174882 | 7/2006 |

* cited by examiner

*Primary Examiner* — Matthew J Kasztejna
(74) *Attorney, Agent, or Firm* — Ostrolenk Faber LLP

(57) ABSTRACT

A gas supply source for supplying gas and a channel along which the gas is supplied can be easily switched by providing an instrument channel for passing an endoscope treating tool, a gas and water supply channel for supplying carbon dioxide etc. to the inside of a body, a gas supply source for a visceral cavity capable of supplying gas at a predetermined pressure, a gas supply source for a lumen capable of supplying gas at an optional pressure, and a switch device for switching from any of and an instrument channel and a gas and water supply channel to any of the gas supply source for a visceral cavity and the gas supply source for a lumen.

9 Claims, 7 Drawing Sheets

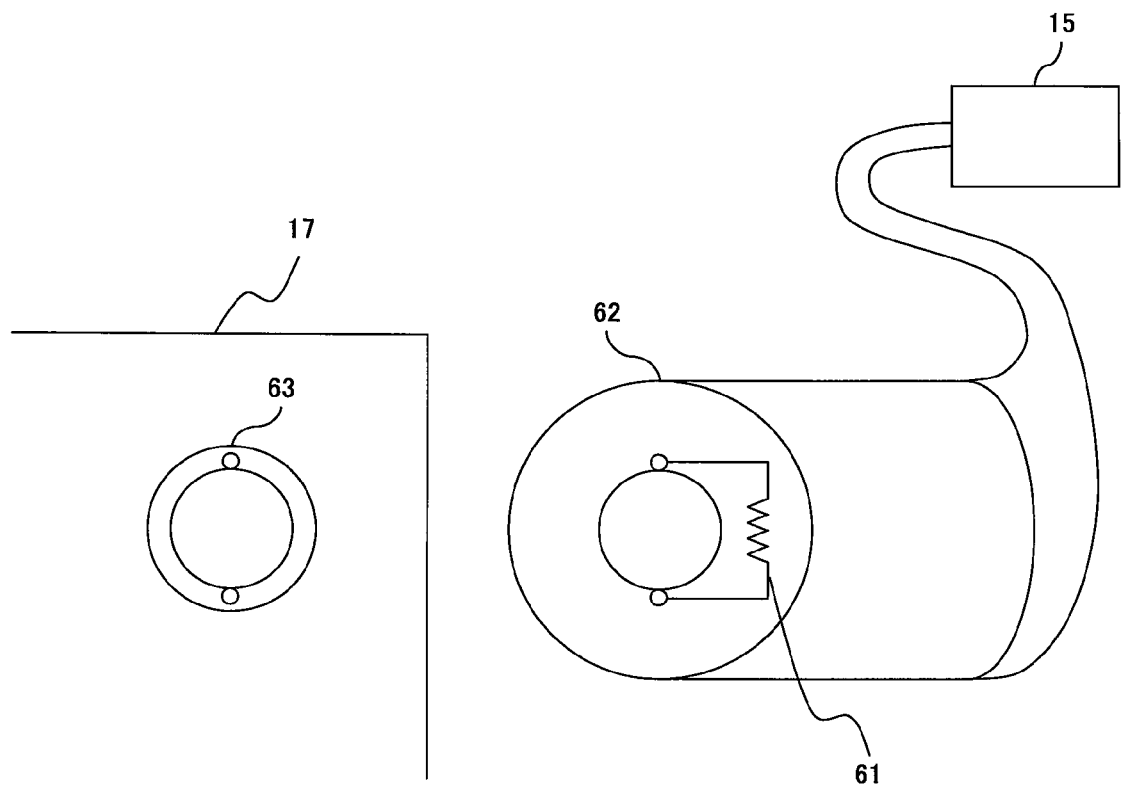
F I G. 6

ENDOSCOPE APPARATUS

BACKGROUND OF THE INVENTION

1. Field of the Invention

The present invention relates to an endoscope apparatus, and more specifically to an endoscope apparatus capable of easily switching gas supplied from a gas supply source for supplying gas to a lumen or a gas supply source for supplying gas to a visceral cavity.

2. Description of the Related Art

Conventionally, a surgery is widely performed using a laparoscopy as a type of endoscope. The endoscope operation can perform treating procedures without laparotomy with a view to minimizing the invasion into a patient.

The endoscope operation is performed by inserting an endoscope insertion unit having a hard endoscope for an observation, a treating tool for performing treating procedures, etc. into the belly of a patient. During the operation, to secure the view of the hard endoscope and secure the area for operation of the treating tool, for example, a blower for supplying a carbon dioxide gas etc. as a blow gas to a visceral cavity is used.

Recently, a NOTES (natural orifice transluminal endoscopic surgery) manipulation for performing an endoscope operation through a mouth, a stomach, a rectum, a vagina, etc. without hurting the skin of a patient has been used. The NOTES manipulation is performed by inserting an endoscope insertion unit from a mouse etc., boring the wall of the tissue of the lumen of a stomach, a large bowel, etc., inserting the endoscope insertion unit from a bored hole into the visceral cavity and performing a necessary treatment.

In proceeding with the NOTES manipulation, a scope is inserted by expanding a lumen and a visceral cavity with supplied gas in the lumen and the visceral cavity. In the lumen, gas is supplied through an instrument channel or a gas and water supply channel of the endoscope insertion unit from a gas supply source for expanding the lumen. In the visceral cavity, gas is supplied through an instrument channel or a gas and water supply channel of the endoscope insertion unit from the gas supply source for expanding the visceral cavity. Therefore, when the endoscope insertion unit is moved between the lumen and the visceral cavity, it is necessary to switch the channels and the gas supply sources.

SUMMARY OF THE INVENTION

According to an aspect of the present invention, the endoscope apparatus of the present invention includes: an endoscope insertion unit to be inserted into a body; a first pipe path, provided in the endoscope insertion unit, for passing an endoscope treating tool; a second pipe path, provided in the endoscope insertion unit, for supplying gas and a liquid in a tank to the body; a first gas supply device capable of supplying gas at a predetermined pressure or a predetermined flow rate; a second gas supply device capable of supplying gas at an optional pressure or an optional flow rate; and a switch unit, provided between the first pipe path and the second pipe path, and between the first gas supply device and the second gas supply device, for switching supply of gas from one of the first gas supply device and the second gas supply device to one of the first pipe path and the second pipe path.

BRIEF DESCRIPTION OF THE DRAWINGS

FIG. 6 is an explanatory view of the fourth embodiment according to the present invention.

DESCRIPTION OF THE PREFERRED EMBODIMENTS

The embodiments of the present invention are described below with reference to the attached drawings.

First described is the outline of the present invention.

Figure 1:
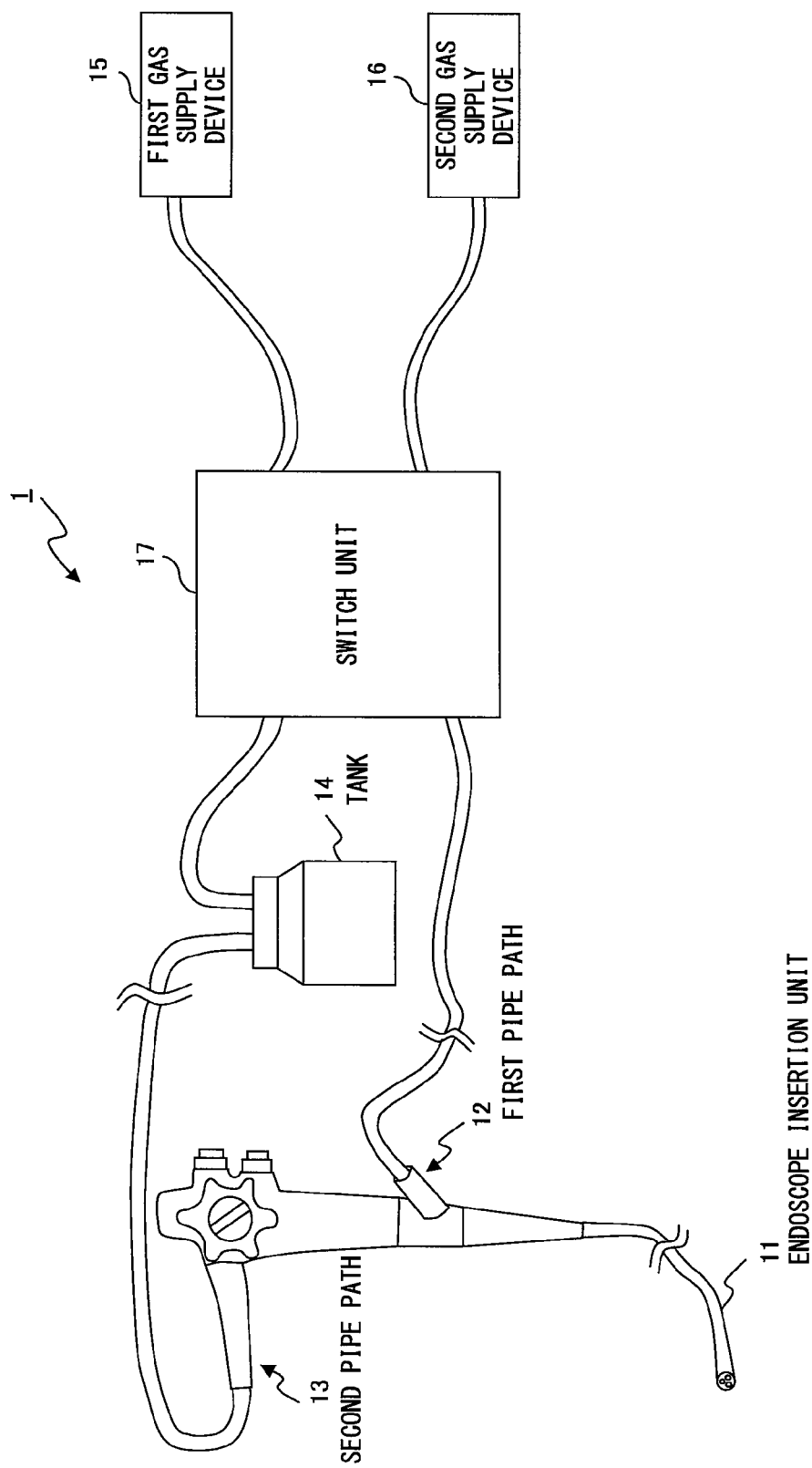
FIG. 1 shows the outline of the present invention.

FIG. 1 shows the outline of the present invention.

In FIG. 1, an endoscope apparatus 1 according to the present invention includes an endoscope insertion unit 11, a first pipe path 12, a second pipe path 13, a tank 14, a first gas supply device 15, a second gas supply device 16, and a switch unit 17.

The endoscope insertion unit 11 is inserted into the body of a patient when an operator as a doctor observes the inside of the body of a patient and performs a treatment on the entrails of a patient.

The first pipe path 12 is called, for example, an instrument channel, provided in the endoscope insertion unit 11, and functions as a pipe path for passing an endoscope treating tool. The first pipe path 12 can pass a liquid such as a chemical solution, a physiological saline, etc. through the body of a patient in the state in which the endoscope treating tool is inserted.

The second pipe path 13 is called, for example, a gas and water supply channel, provided in combination with the first pipe path 12 in the endoscope insertion unit 11, and functions as a pipe path for supplying gas such as air, carbon dioxide, etc., liquid such as a physiological saline etc., or a mixture of the gas and the liquid to the body of a patient. The supplied gas is transmitted from the first gas supply device 15 or the second gas supply device 16. However, the supplied liquid is stored in the tank 14, and provided for the inside of the body by the pressure etc. of the gas transmitted from the first gas supply device 15 or the second gas supply device 16. The supplied mixture is obtained by mixing the liquid stored in the tank 14 with the gas transmitted from the first gas supply device 15 or the second gas supply device 16, and supplied to the inside of the body.

The first gas supply device 15 is called, for example, a gas supply source for a visceral cavity provided for a blower, and can supply gas by a predetermined pressure or a predetermined flow rate.

The second gas supply device 16 is called, for example, a gas supply source for a lumen, and cal supply gas by an optional or an optional flow rate.

The switch unit 17 is provided between the first pipe path 12 and the second pipe path 13, and between the first gas supply device 15 and the second gas supply device 16. The switch unit 17 switches the supply of gas from one of the first gas supply device 15 and the second gas supply device 16 to one of the first pipe path 12 and the second pipe path 13. For example, the switch unit 17 switches the supply of gas from the supply from the 15 to the first pipe path 12 to the supply from the second gas supply device 16 to the first pipe path 12. The switch unit 17 is described later in detail.

Next, the first embodiment according to the present invention is described below.

Figure 2:
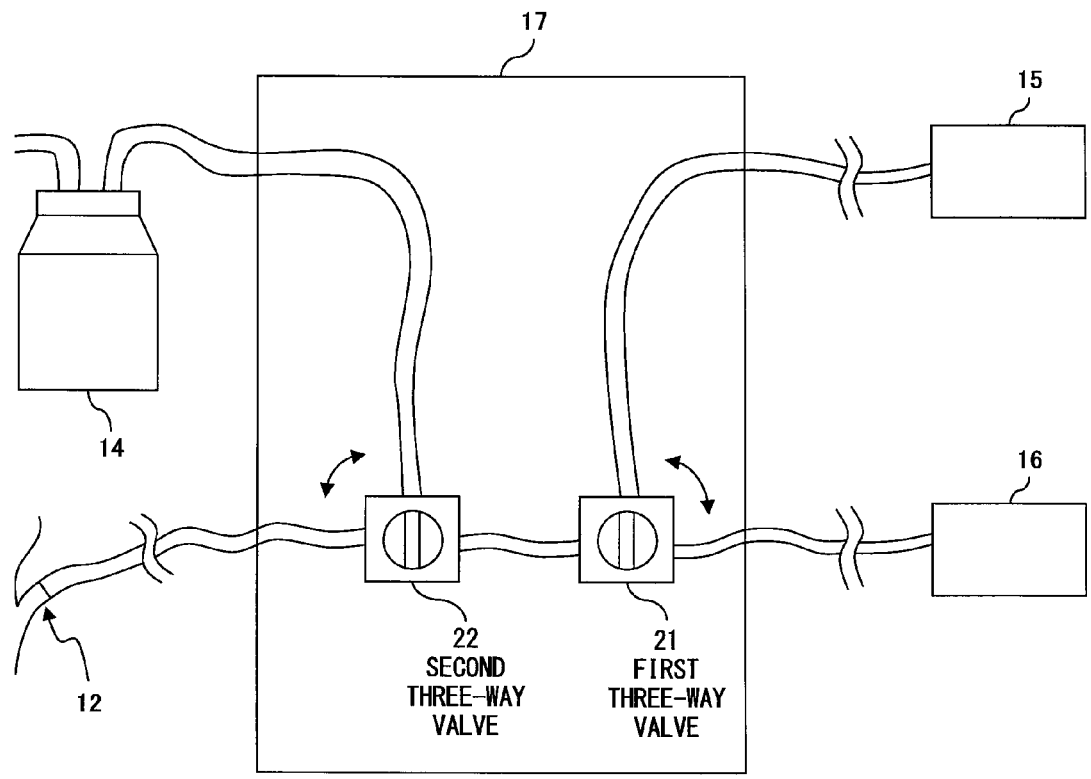
FIG. 2 is an explanatory view of the first embodiment according to the present invention.

FIG. 2 is an explanatory view of the first embodiment of the present invention.

In the first embodiment according to the present invention, the endoscope apparatus 1 includes the endoscope insertion unit 11, the first pipe path 12, the second pipe path 13, the tank 14, the first gas supply device 15, the second gas supply device 16, and the switch unit 17 as described above with reference to FIG. 1. As shown in FIG. 2, the switch unit 17 is provided with two three-way valves, that is, a first three-way valve and a second three-way valve. The three-way valve has a mechanism structure for connection from one supply system to one of two exhaust systems.

The first three-way valve 21 switches the supply of gas from one of the first gas supply device 15 and the second gas supply device 16 in the direction of the second three-way valve. The second three-way valve is provided between the first pipe path 12 and the second pipe path 13 and the first three-way valve 21, and switches the gas supplied from the first three-way valve to one of the first pipe path 12 and the second pipe path 13. For example, when the endoscope insertion unit 11 is moved from a lumen into a visceral cavity in the NOTES manipulation, it is necessary to switch from the state in which gas is supplied from the second gas supply device 16 to the first pipe path 12 to the state in which it is supplied from the first gas supply device 15 to the first pipe path 12. At this time, the supply of gas can be easily switched from the second gas supply device 16 to the first gas supply device 15 only by operating the first three-way valve 21.

Described next is the second embodiment of the present invention.

Figure 3:
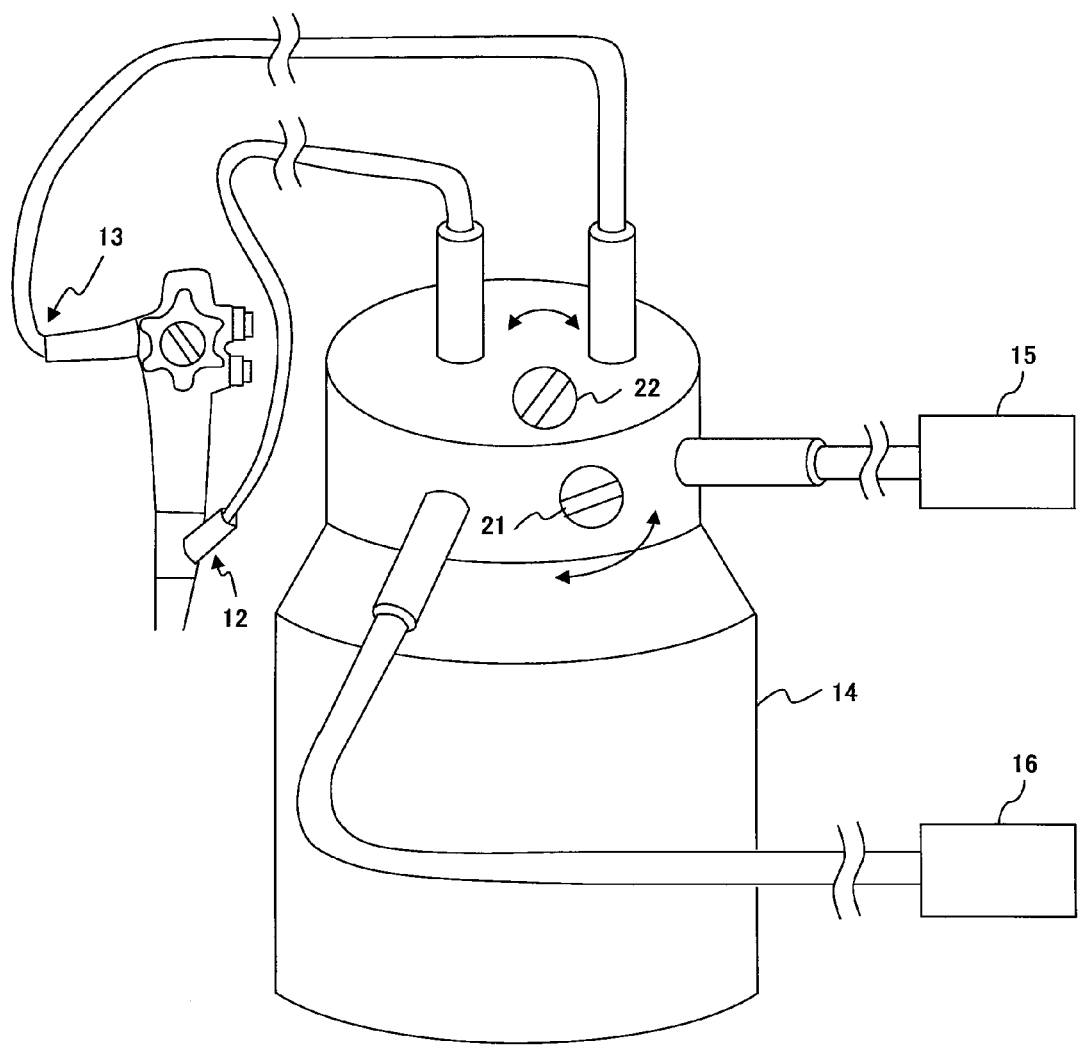
FIG. 3 is an explanatory view of the second embodiment according to the present invention.

FIG. 3 is an explanatory view of the second embodiment according to the present invention.

In the second embodiment according to the present invention, the endoscope apparatus 1 includes the endoscope insertion unit 11, the first pipe path 12, the second pipe path 13, the tank 14, the first gas supply device 15, the second gas supply device 16, and the switch unit 17 described above with reference to FIG. 1. As shown in FIG. 3, the switch unit 17 is provided with two three-way valves, that is, a first three-way valve and a second three-way valve, and stored in the tank 14.

Described next is the third, fourth, and fifth embodiments according to the present invention.

Figure 4:
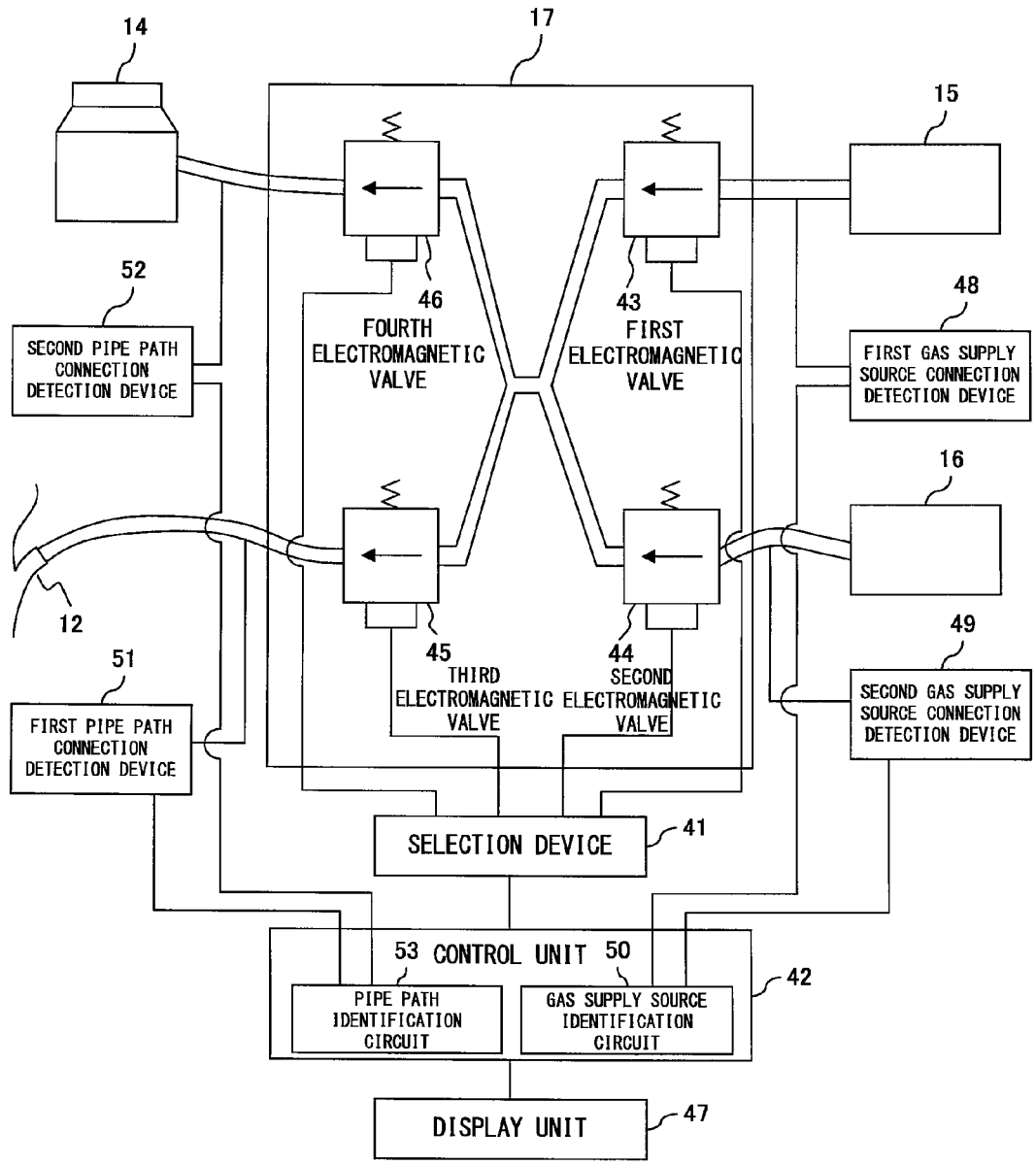
FIG. 4 is an explanatory view of the third, fourth, and fifth embodiments according to the present invention.

FIG. 4 is an explanatory view of the third, fourth, and fifth embodiments according to the present invention.

First described below is the third embodiment according to the present invention.

In the third embodiment according to the present invention, the endoscope apparatus 1 includes the endoscope insertion unit 11, the first pipe path 12, the second pipe path 13, the tank 14, the first gas supply device 15, the second gas supply device 16, and the switch unit 17 described above with reference to FIG. 1, and additionally a selection device 41, a control unit 42, and a display unit 47.

The selection device 41 selects one of the first gas supply device 15 and the second gas supply device 16, and also selects one of the first pipe path 12 and the second pipe path 13. The control unit 42 controls the switch unit 17 depending on the output from the selection device 41. As shown in FIG. 4, the switch unit 17 is provided with a first electromagnetic valve 43, a second electromagnetic valve 44, a third electromagnetic valve 45, and a fourth electromagnetic valve 46. The three-way electromagnetic valve is used in connection from one supply system to one of the two exhaust systems, and has a system of opening and closing an iron chip called a plunger using the magnetism of an electromagnet (solenoid).

The first electromagnetic valve 43 is connected to the first gas supply device 15, and turns on and off the supply of gas from the first gas supply device 15. The second electromagnetic valve 44 is connected to the second gas supply device 16, and turns on and off the supply of gas from the second gas supply device 16. The third electromagnetic valve 45 is provided between the first pipe path 12, and the first electromagnetic valve 43 and the second electromagnetic valve 44, and turns on and off the supply of gas to the first pipe path 12. The fourth electromagnetic valve 46 is provided between the second pipe path 13, and the first electromagnetic valve 43 and the second electromagnetic valve 44, and turns on and off the supply of gas to the second pipe path 13. The control unit 42 turns on and off the supply of gas by the first electromagnetic valve 43, the second electromagnetic valve 44, the third electromagnetic valve 45, and the fourth electromagnetic valve 46 depending on the output from the selection device 41.

The display unit 47 is, for example, a touch panel, and displays the operation state information indicating whether or not the first gas supply device 15 is supplying gas, the second gas supply device 16 is supplying gas, the supply of gas is performed to the first pipe path 12, and the supply of gas is performed to the second pipe path 13.

Figure 5:
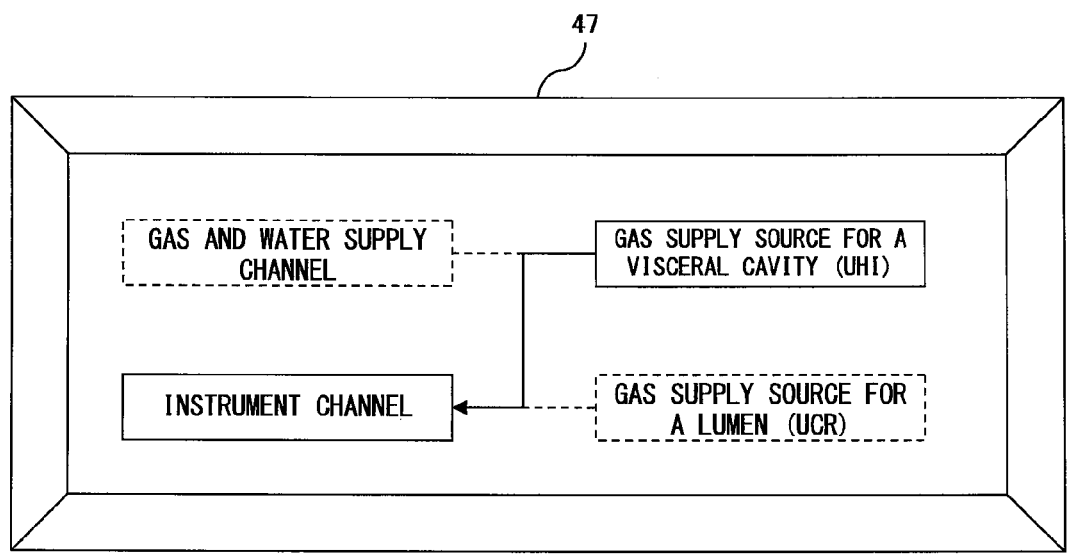
FIG. 5 shows an example of displaying a touch panel.

FIG. 5 shows an example of the display of a touch panel.

As shown in FIG. 5, the touch panel as the display unit 47 displays the operation state information indicating whether or not the first gas supply device 15 is supplying gas. The operable state shown in FIG. 5 indicates that the first gas supply device 15 as a "gas supply source for a visceral cavity (UHI)" is supplying gas, and the gas is supplied to the first pipe path 12 as an "instrument channel".

Then, the selection device 41 can selects the supply of gas from the first gas supply device 15 or the second gas supply device 16, and the supply of gas to the first pipe path 12 or the second pipe path 13 on the touch panel.

Described next is the fourth embodiment according to the present invention.

The configuration shown in FIG. 4 is described below.

In the fourth embodiment according to the present invention, the endoscope apparatus 1 further includes a first gas supply source connection detection device 48, a second gas supply source connection detection device 49, a gas supply source identification circuit 50, a first pipe path connection detection device 51, a second pipe path connection detection device 52, and a pipe path identification circuit 53 in addition to the endoscope insertion unit 11, the first pipe path 12, the second pipe path 13, the tank 14, the first gas supply device 15, the second gas supply device 16, the switch unit 17, the selection device 41, the control unit 42, and the display unit 47.

The first gas supply source connection detection device 48 detects whether or not the first gas supply device 15 is connected to the first electromagnetic valve 43. The second gas supply source connection detection device 49 detects whether or not the second gas supply device 16 is connected to the second electromagnetic valve 44. The detection is performed on the basis of an electric resistance value.

FIG. 6 is an explanatory view of the fourth embodiment according to the present invention.

That is, as shown in FIG. 6, the first gas supply source connection detection device 48 is a first resistor 61 for detecting whether or not the first gas supply device 15 is connected to the first electromagnetic valve 43 by detecting the electric resistance value between two electrodes. Practically, by connecting a connection portion 62 of the first gas supply device 15 to a connection portion 63 of the switch unit 17 provided with the first electromagnetic valve 43, the first resistor 61 detects a resistance value.

Similarly, the second gas supply source connection detection device 49 is a second resistor for detecting whether or not the second gas supply device 16 is connected to the second electromagnetic valve 44 by detecting an electric resistance value between two electrodes.

The gas supply source identification circuit 50 identifies which is connected to each connection port provided for the switch unit 17, the first gas supply device 15 or the second gas supply device 16 on the basis of the detection results of the first gas supply source connection detection device 48 and the second gas supply source connection detection device 49. In this case, the control unit 42 associates the switch unit 17 with the first gas supply device 15 and the second gas supply device 16 depending on the output from the gas supply source identification circuit 50. To be more concrete, the control unit 42 associates the first electromagnetic valve 43 (first switch device) and the second electromagnetic valve 44 (second switch device) provided for the switch unit 17 with the first gas supply device 15 and the second gas supply device 16. For example, the control unit 42 associates the first electromagnetic valve 43 with the first gas supply device 15, and associates the second electromagnetic valve 44 with the second gas supply device 16.

According to the association, it can be determined whether the gas supply source connected to the switch unit 17 is the first gas supply device 15, for example, a gas supply source for a visceral cavity provided for the blower or the second gas supply device 16, for example, a gas supply source for a lumen. Thus, although a connection is made to the switch unit 17 incorrectly from the first gas supply device 15 or the second gas supply device 16 using an incorrect connection port, a gas supply source can be correctly opened on the display unit 47 as a touch panel.

In addition, like the first gas supply source connection detection device 48 shown in FIG. 6, the first pipe path connection detection device 51 is a third resistor for detecting whether or not the first pipe path 12 is connected to the third electromagnetic valve 45 by detecting the electric resistance value between two electrodes. Furthermore, like the first gas supply source connection detection device 48 shown in FIG. 6, the second pipe path connection detection device 52 is a fourth resistor for detecting whether or not the second pipe path 13 is connected to the fourth electromagnetic valve 46 by detecting an electric resistance value between two electrodes.

Furthermore, the first pipe path connection detection device 51 detects whether or not the first pipe path 12 is connected to the third electromagnetic valve 45, and the second pipe path connection detection device 52 detects whether or not the second pipe path 13 is connected to the fourth electromagnetic valve 46. The pipe path identification circuit 53 identifies which is connected to each connection port provided for the switch unit 17, the first pipe path 12 or the second pipe path 13 on the basis of the detection results of the first pipe path connection detection device 51 and the second pipe path connection detection device 52. At this time, the control unit 42 associates the switch unit 17 with the first pipe path 12 and the second pipe path 13 depending on the output from the pipe path identification circuit 53. To be more concrete, the control unit 42 associates the third electromagnetic valve 45 (third switch device) and the fourth electromagnetic valve 46 (fourth switch device) provided for the switch unit 17 with the first pipe path 12 and the second pipe path 13. For example, the control unit 42 associates the third electromagnetic valve 45 with the first pipe path 12, and associates the fourth electromagnetic valve 46 with the second pipe path 13.

On the basis of the association, it is possible to determine to which the pipe path is connected, the first pipe path 12 or the second pipe path 13. Thus, although a connection is made to the switch unit 17 incorrectly from the first pipe path 12 or the second pipe path 13 using an incorrect connection port, a pipe path can be correctly opened on the display unit 47 as a touch panel.

Finally described below is the fifth embodiment according to the present invention.

Figure 7:
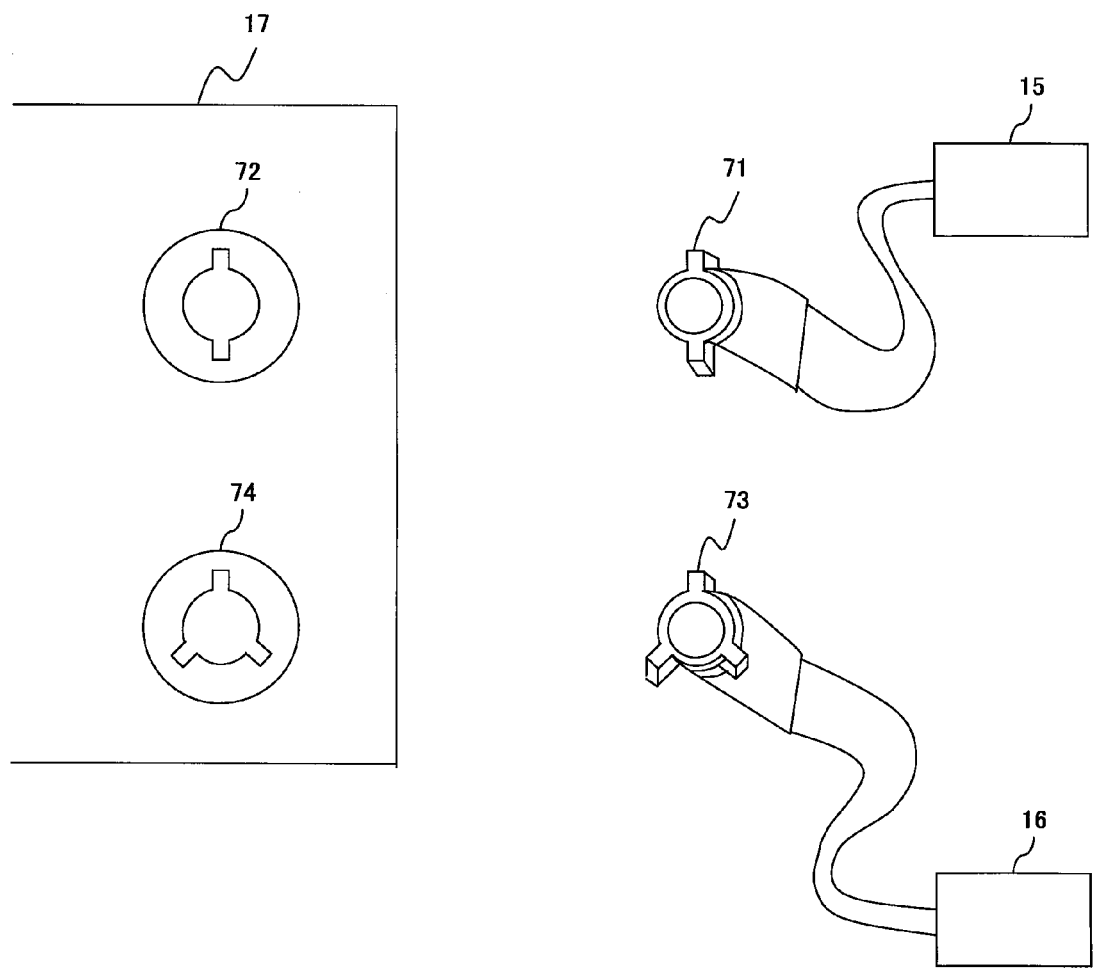
FIG. 7 is an explanatory view of the fifth embodiment according to the present invention.

FIG. 7 is an explanatory view of the fifth embodiment according to the present invention.

The fifth embodiment according to the present invention perform detection depending on the shape of a connection portion instead of the detection of a resistance value by a resistor according to the fourth embodiment described with reference to FIG. 6.

As shown in FIG. 7, a connection portion 71 of the first gas supply device 15 has two projections to be engaged in a connection portion 72 of the first electromagnetic valve 43 having two notches. In addition, a connection portion 73 of the second gas supply device 16 has three projections to be engaged in a connection portion 74 of the second electromagnetic valve 44 having three notches. The connection portion 71 of the first gas supply device 15 having two projections cannot be engaged in shape with the connection portion 74 of the second electromagnetic valve 44 having three notches. In addition, the second gas supply device 16 having three projections cannot be engaged in shape with the first electromagnetic valve 43 having two notches.

That is, the first gas supply source connection detection device 48 detects that the first gas supply device 15 is connected to the first electromagnetic valve 43 by engaging the first gas supply device 15 with the first electromagnetic valve 43. The second gas supply source connection detection device 49 detects that the second gas supply device 16 is connected to the second electromagnetic valve 44 by engaging the second gas supply device 16 with the second electromagnetic valve 44.

Similarly, the connection portions of the first pipe path 12 and the third electromagnetic valve 45 can be engaged in shape with each other. The connection portions of the second pipe path 13 and the fourth electromagnetic valve 46 can be engaged in shape with each other. The first pipe path 12 and the fourth electromagnetic valve 46 cannot be engaged in shape with each other. The second pipe path 13 and the third electromagnetic valve 45 cannot be engaged in shape with each other. The first pipe path connection detection device 51 detects that the first pipe path 12 is connected to the third electromagnetic valve 45 by engaging the first pipe path 12 with the third electromagnetic valve 45. The second pipe path connection detection device 52 detects that the second pipe path 13 is connected to the fourth electromagnetic valve 46 by engaging the second pipe path 13 with the fourth electromagnetic valve 46.

Each of the embodiments according to the present invention is described above with reference to the attached drawings, but the endoscope apparatus according to the present invention is not limited to the above-mentioned embodiments so far as the functions are realized in various configurations within the gist of the present invention.

For example, the switch unit 17 is not limited to a three-way valve or an electromagnetic valve, but has only to have the functions of connecting one supply system (first gas supply device 15 or second gas supply device 16) to two exhaust systems (first pipe path 12 and second pipe path).

The detection by the first gas supply source connection detection device 48 etc. as to whether or not the first gas supply device 15 etc. is connected can be not only the detection of a resistance value by a resistor or the detection by the shape of a connection portion, but also the detection by the thickness of a connection portion.

What is claimed is:

1. An endoscope apparatus, comprising:
   an endoscope insertion unit to be inserted into a body;
   a first pipe path, provided in the endoscope insertion unit, for passing an endoscope treating tool;
   a second pipe path, provided in the endoscope insertion unit, for supplying gas and a liquid in a tank to the body;
   a first gas supply device capable of supplying gas at a predetermined pressure or a predetermined flow rate;
   a second gas supply device capable of supplying gas at an optional pressure or an optional flow rate;
   a switch unit, provided between the first pipe path and the second pipe path, and between the first gas supply device and the second gas supply device, for switching supply of gas from one of the first gas supply device and the second gas supply device to one of the first pipe path and the second pipe path;
   a selection device selecting one of the first gas supply device and the second gas supply device, and selecting one of the first pipe path and the second pipe path; and
   a control unit controlling the switch unit depending on output from the selection device, wherein
   the switch unit comprises:
      a first electromagnetic valve, connected to the first gas supply device, for turning on and off supply of gas from the first gas supply device;
      a second electromagnetic valve, connected to the second gas supply device, for turning on and off supply of gas from the second gas supply device;
      a third electromagnetic valve, provided between the first pipe path, and the first electromagnetic valve and the second electromagnetic valve, for turning on and off supply of gas to the first pipe path; and
      a fourth electromagnetic valve, provided between the second pipe path, and the first electromagnetic valve and the second electromagnetic valve, for turning on and off supply of gas to the second pipe path, and
   the control unit turns on and off supply of gas using the first electromagnetic valve, the second electromagnetic valve, the third electromagnetic valve, and the fourth electromagnetic valve.

2. The apparatus according to claim 1, further comprising a display unit displaying operation state information indicating whether or not the first gas supply device is supplying gas, whether or not the second gas supply device is supplying gas, whether or not gas is being supplied to the first pipe path, and whether or not gas is being supplied to the second pipe path.

3. The apparatus according to claim 2, wherein the display unit is a touch panel, and the selection device can select supply of gas from the first gas supply device or the second gas supply device, and can select supply of gas to the first pipe path or the second pipe path on the touch panel.

4. The apparatus according to claim 2, further comprising:
   a first gas supply source connection detection device detecting whether or not the first gas supply device is connected to the first electromagnetic valve;
   a second gas supply source connection detection device detecting whether or not the second gas supply device is connected to the second electromagnetic valve; and
   a gas supply source identification circuit identifying which is connected to each connection port provided for the switch unit, the first gas supply device or the second gas supply device, on a basis of detection results of the first gas supply source connection detection device and the second gas supply source connection detection device, wherein
   a first switch device and a second switch device in the switch unit are associated with the first gas supply device and the second gas supply device depending on output from the gas supply source identification circuit.

5. The apparatus according to claim 4, wherein:
   the first gas supply source connection detection device is a first resistor detecting whether or not the first gas supply device is connected to the first electromagnetic valve by detecting an electric resistance value between two electrodes; and
   the second gas supply source connection detection device is a second resistor detecting whether or not the second gas supply device is connected to the second electromagnetic valve 44 by detecting an electric resistance value between two electrodes.

6. The apparatus according to claim 4, wherein:
   connection portions of the first gas supply device and the first electromagnetic valve can be engaged in shape with each other, connection portions of the second gas supply device and the second electromagnetic valve can be engaged in shape with each other, the first gas supply device and the second electromagnetic valve cannot be engaged in shape with each other, and the second gas supply device and the first electromagnetic valve cannot be engaged in shape with each other;
   the first gas supply source connection detection device detects that the first gas supply device is connected to the first electromagnetic valve by engaging the first gas supply device with the first electromagnetic valve; and
   the second gas supply source connection detection device detects that the second gas supply device is connected to the second electromagnetic valve by engaging the second gas supply device with the second electromagnetic valve.

7. The apparatus according to claim 2, further comprising:
   a first pipe path connection detection device detecting whether or not the first pipe path is connected to the third electromagnetic valve;
   a second pipe path connection detection device detecting whether or not the second pipe path is connected to the fourth electromagnetic valve; and
   a pipe path identification circuit which is connected to each connection port provided for the switch unit, the first pipe path or the second pipe path, on the basis of detection results of the first pipe path connection detection device and the second pipe path connection detection device, wherein
   a third switch device and a fourth switch device in the switch unit are associated with the first pipe path and the second pipe path depending on output from the pipe path identification circuit.

8. The apparatus according to claim 7, wherein:
the first pipe path connection detection device is a third resistor for detecting whether or not the first pipe path is connected to the third electromagnetic valve by detecting an electric resistance value between two electrodes; and
the second pipe path connection detection device is a fourth resistor for detecting whether or not the second pipe path is connected to the fourth electromagnetic valve by detecting an electric resistance value between two electrodes.

9. The apparatus according to claim 7, wherein;
connection portions of the first pipe path and the third electromagnetic valve can be engaged in shape with each other, connection portions of the second pipe path and the fourth electromagnetic valve can be engaged in shape with each other, the first pipe path and the fourth electromagnetic valve cannot be engaged in shape with each other, and the second pipe path and the third electromagnetic valve cannot be engaged in shape with each other;
the first pipe path connection detection device detects that the first pipe path is connected to the third electromagnetic valve by engaging the first pipe path with the third electromagnetic valve; and
the second pipe path connection detection device detects that the second pipe path is connected to the fourth electromagnetic valve by engaging the second pipe path with the fourth electromagnetic valve.

* * * * *